United States Patent [19]

Zemlyakova

[11] 4,292,307
[45] Sep. 29, 1981

[54] VACCINE AND METHOD FOR PROPHYLAXIS AND TREATMENT OF CLOSTRIDIOSES OF ANIMALS AND POULTRY

[76] Inventor: Valentina P. Zemlyakova, ulitsa Jugo-Zapadnaya, dom 73/26, kv. 48, Minsk, U.S.S.R.

[21] Appl. No.: 122,172

[22] Filed: Feb. 19, 1980

Related U.S. Application Data

[63] Continuation of Ser. No. 942,145, Sep. 14, 1978, abandoned.

[30] Foreign Application Priority Data

Sep. 30, 1977 [SU] U.S.S.R. .............................. 2523702

[51] Int. Cl.³ ....................... A61K 9/12; A61K 39/08; A61K 39/116
[52] U.S. Cl. ..................................................... 424/92
[58] Field of Search ......................................... 424/92

[56] References Cited

U.S. PATENT DOCUMENTS

| 2,705,214 | 3/1955 | Hink | 424/92 |
| 2,719,102 | 9/1955 | Baldwin | 424/92 |
| 3,083,142 | 3/1963 | Howell et al. | 424/92 |
| 3,288,680 | 11/1966 | Sterne | 424/92 |
| 3,579,633 | 5/1971 | Thomson | 424/92 |

FOREIGN PATENT DOCUMENTS

| 288934 | 12/1965 | Australia | 424/92 |
| 895073 | 5/1962 | United Kingdom | 424/92 |
| 898783 | 6/1962 | United Kingdom | 424/92 |
| 901433 | 7/1962 | United Kingdom | 424/92 |
| 947912 | 1/1964 | United Kingdom | 424/92 |
| 958574 | 5/1964 | United Kingdom | 424/92 |

*Primary Examiner*—Shep K. Rose
*Attorney, Agent, or Firm*—Robert E. Burns; Emmanuel J. Lobato; Bruce L. Adams

[57] ABSTRACT

A vaccine for prophylaxis and treatment of clostridioses of animals and poultry is provided which comprises toxoids of *Clostridium perfringens* types A, B and D, *Cl. oedematiens*, and *Cl. septicum*, separated from the microbeal mass, a sorbent, and a solvent, the antigenic activity of said toxoids, expressed in combining units per ml of the vaccine, being as follows:

| toxoid of *Cl. perfringens* type A | 2–100 |
| toxoid of *Cl. perfringens* type B | 2–100 |
| toxoid of *Cl. perfringens* type D | 1–80 |
| toxoid of *Cl. oedematiens* | 1–80 |
| toxoid of *Cl. septicum* | 2–100 |
| sorbent | 1–10 mg |
| solvent | balance. |

Prophylaxis and treatment of clostridioses of animals and poultry is carried out by giving said animals and poultry parenterally 0.5 to 5 ml of the vaccine, from one to three times, the vaccine comprising toxoids of *Clostridium perfringens* types A, B, and D, *Cl.oedematiens*, and *Cl.septicum*, a sorbent and a solvent, the antigenic activity of said toxoids, expressed in combining units per ml of the vaccine, being as follows:

| toxoid of *Cl. perfringens* type A | 2–100 |
| toxoid of *Cl. perfringens* type B | 2–100 |
| toxoid of *Cl. perfringens* type D | 1–80 |
| toxoid of *Cl. oedematiens* | 1–80 |
| toxoid of *Cl. septicum* | 2–100 |
| sorbent | 1–10 mg |
| solvent | balance. |

The vaccine is universal and can be used at large industrialized animal and poultry farms to protect animals and birds from 5–11 causative agents that are widely spread in nature and are the cause of considerable economic damage.

12 Claims, No Drawings

VACCINE AND METHOD FOR PROPHYLAXIS AND TREATMENT OF CLOSTRIDIOSES OF ANIMALS AND POULTRY

This is a continuation of application Ser. No. 942,145, filed Sept. 14, 1978, now abandoned.

FIELD OF THE INVENTION

The present invention relates to veterinary microbiology and more particularly it relates to a vaccine for prophylaxis and treatment of clostridiosis in animals and birds.

BACKGROUND OF THE INVENTION

A a polyvalent antigenic vaccine against clostridioses of animals, is known comprising antigens that are anacultures of Cl. perfringens types B, C, and D, *Cl. oedematiens, Cl. septicum, Cl. tetani,* and *Cl. chauvoei,* a mineral oil, a nonionic lipophilic emulsifying agent, and a nonionic hydrophilic emulsifying agent.

The presence of microbial cells in the vaccine produces a negative effect on detoxification and purification of the preparation to reduce its antigenic and immunogenic power, to increase the reactogenecity, and produces mainly antimicrobial immunity in the vaccinated animals.

A precipitated toxoid-vaccine is also known which contains a toxoid of *Cl. perfringens* type A, anacultures *Cl. perfringens* types B, C, and D, *Cl. oedematiens,* and *Cl. septicum* separated from the microbial mass. Alumina gel is used as an adsorbent. The activity of the toxoid of *Cl. perfringens* type A is measured in combining units per ml of the vaccine and is equal to 20 units.

The number of combining units characterizes the antigenic and immunogenic properties of the toxoid.

A combining unit is the quantity of the test toxoid (at various stages of its preparation), capable of combining with one antitoxic unit of specific serum. The specific activity of toxoids, expressed in combining units, is determined by the method proposed by G. P. Cherkas (1958) and I. M. Khaustova (1959).

The activity of each toxin of the starting cultures that are constituents of said vaccine is determined by the MLD (minimum lethal dose) and is, on an average, 400–1000 MLD in one ml of the vaccine (for albino mice).

The antigenic and immunogenic properties of the preparation are insufficiently strong, and it exhibits, mainly, antimicrobial immunity and a very weak antitoxic immunity against *Clostridium perfringens* types B, C, and D, *Cl. oedematiens* and *Cl. septicum.*

The vaccinated animals develop immunity very slowly, and it lasts for a short time: the immunity sharply weakens in 1–2 months, which involves repeated vaccinations with increased doses of the preparation.

A another vaccine, namely ditoxoid, is also known which is intended for specific prophylaxis of enterotoxemia of calves. The preparation includes toxoids of *Clostridium perfringens* types A and D, separated from the microbial mass, their antigenic activity being 100 combining units of each toxoid per ml, as well as a sorbent and a solvent. The sorbent used in the vaccine in alumina gel and the solvent, a physiological salt solution.

Said preparation cannot be used for treatment and prophylaxis of diseases caused by a combination of widely spread natural microorganisms of the genus Clostridium since it contains toxoids effective only against two causative agents.

SUMMARY OF THE INVENTION

The principal object of the invention is to improve the antigenic and immunogenic properties of the vaccine and to provide strong antitoxic immunity in vaccinated animals.

Another object of the invention is to provide a universal and stable vaccine against a combination of most widely spread microorganisms of the genus Clostridium.

The present invention resides in that a vaccine for prophylaxis and treatment of clostridiosis of animals and poultry comprises toxoids of *Clostridium perfringens* types A, B, and D, *Cl. oedematiens, Cl. septicum,* separated from the microbial mass, a sorbent and a solvent, the antigenic activity of said toxoids, expressed in binding units per ml of the vaccine, being as follows:

| | |
|---|---|
| toxoid of *Cl. perfringens* type A | 2–100 |
| toxoid of *Cl. perfringens* type B | 2–100 |
| toxoid of *Cl. perfringens* type D | 1–80 |
| toxoid of *Cl. oedematiens* | 1–80 |
| toxoid of *Cl. septicum* | 2–100 |
| sorbent | 1–10 mg |
| solvent | balance. |

Said vaccine is used against the following diseases of cattle, horses, sheep, pigs, commercial animals and poultry: gas gangrene, malignant edema, endometritis, vaginitis, mastitis, miscarriage, bradzot of sheep, and enterotoxemia of the younger livestock, that are produced by said caustive agents.

It is not recommended to use the vaccine in which the antigenic activity of its components is below the minimum doses since the vaccine will fail to produce the antitoxic immunity in the vaccinated animals and birds at the protective level.

Nor is it recommended to use the vaccine in which the antigenic activity of its components is higher than their maximum doses, since the production of antitoxins in the vaccinated animals is inhibited in excess (antitoxic immunity).

It is recommended that the vaccine also contain a toxoid of *Cl. tetani,* separated from the microbial mass, its antigenic activity, expressed in combining unit per ml of the vaccine, being 1–80.

The proposed vaccine is used against infectious enterotoxemia in young animals, mainly newborns of all agricultural animals and poultry, in female adults of cattle, horses, sheep, pigs, against gynaecological diseases (endometritis, vaginitis, mastitis), wound complications, gas gangrene, malignant edema, bradzot, of sheep, that are caused by said combination of microorganisms of the genus Clostridium. It is recommended that the vaccine also contain toxoids of *Cl. botulinum* of at least two of the types A, B, C, D, E, and F, separated from the bacterial mass, their antigenic activity, expressed in combining units per ml of the vaccine, being as follows:

| | |
|---|---|
| toxoid of *Cl. botulinum* type A | 2–100 |
| toxoid of *Cl. botulinum* type B | 0.2–80 |
| toxoid of *Cl. botulinum* type C | 0.2–80 |
| toxoid of *Cl. botulinum* type D | 0.2–80 |
| toxoid of *Cl. botulinum* type E | 0.2–80 |

| | |
|---|---|
| -continued | |
| toxoid of Cl. botulinum type F | 0.2–80 |

The proposed vaccine is used for prophylaxis and treatment of forage toxicoinfection, anaerobic enterotoxemia, gynaecological diseases and wound complications.

The incorporation into the vaccine of toxoids of Cl. tetani and Cl. botulinum types A, B, C, D, E, and F is explained by the necessity of prophylaxis and treatment of clostridiosis caused by said microorganisms.

The selection of the minimum and maximum doses of antigenic activity of toxoids of Cl. botulinum and Cl. tetani in the proposed vaccine is governed by the same reasons as specified above for toxoids of Cl. perfringens types A, B, and D, Cl. oedematiens, and Cl. septicum.

It is recommended that the vaccine contain alumina gel as the sorbent. This sorbent ensures complete sorption of the toxoids and does not produce any harmful effect on animals.

It is recommended to use a mixture of a phosphate buffer and a physiological salt solution, taken in the weight ratio of 1:1, as the solvent.

The invention also resides in a method for prophylaxis and treatment of clostridiosis of animals and poultry, consisting in that said animals and poultry are given the vaccine in doses from 0.5 to 5 ml, from one to three times, the vaccine comprising toxoids separated from the microbial cells of Clostridium perfringens, types A, B, and D, Cl. oedematiens, Cl. septicum, a sorbent and a solvent, the antigenic activity of said toxoids, expressed in combining units per ml of the vaccine, being as follows:

| | |
|---|---|
| toxoid of Cl. perfringens, type A | 2–100 |
| toxoid of Cl. perfringens type B | 2–100 |
| toxoid of Cl. perfringens type D | 1–80 |
| toxoid of Cl. oedematiens | 1–80 |
| toxoid of Cl. septicum | 2–100 |
| sorbent | 1–10 mg |
| solvent | balance | with subsequent re-vaccination.

To maintain the immunity at the protective level, the animals should be re-vaccinated once a year or for special indications (infection outbreak).

It is recommended that the animals and poultry be given the vaccine also containing a toxoid of Cl. tetani, separated from the microbial cells, its antigenic activity, expressed in combining unit per ml of the vaccine, being 1–80.

It is also recommended that the animals and poultry be given the vaccine containing a toxoid of Cl. botulinus (separated from the microbial cells) of at least two types out of the types A, B, C, E, and F, their antigenic activity, expressed in combining units per ml of the vaccine, being as follows:

| | |
|---|---|
| toxoid of Cl. botulinus type A | 2–100 |
| toxoid of Cl. botulinus type B | 0.2–80 |
| toxoid of Cl. botulinus type C | 0.2–80 |
| toxoid of Cl. botulinus type F | 0.2–80 |
| toxoid of Cl. botulinus type F | 0.2–80 |

It is recommended to given the vaccine parenterally or in an aerosol form.

DETAILED DESCRIPTION OF THE INVENTION

The proposed vaccine is a liquid preparation that separates on standing into a colorless supernatant liquid and a white, pale-brown, or yellowish precipitate. When shaken, the vaccine gives a homogeneous suspension free from flakes or extraneous impurities.

The vaccine has been tested on smaller laboratory animals and on agricultural animals such as cattle, sheep, pigs, camels, horses, etc., on newborn calves, gilts, lambs, poultry (e.g. hens), and commercial animals (minks).

Observation of the animals has shown that the active formation of intense immunity stimulated the production of a high titer of toxoids to each component of the vaccine, and the vaccinated animals developed immunity (in primary immunization) in 10–25 days and (after re-vaccination) in 5–10 days. The length and activity of the immunity produced by the proposed vaccine were studied on 100 animals that were infected with the corresponding virulent culture or a toxin, which is a constituent of the proposed vaccine, 1,2,4,6,10,12 months after the vaccination and 2,4, and 5 years after the vaccination. Non-immunized animals, and also animals who had the corresponding disease in the past, were used as controls. The animals were selected into the control group according to the analogue principle.

The animals were immunized in accordance with the immunization methods developed by the inventors for each species of animals and poultry.

In cases where one or several said causative agents were revealed, all profitable healthy cattle, calves, pigs, sheep, horses, camels, poultry, minks, and other animals were given a prophylactic vaccination irrespective of the pregnancy term. At affected farms, where the preparation was used for the first time, the cattle, horses, camels, pigs and sheep were vaccinated from one to three times. The vaccine was given in doses from 0.5 to 5 ml, parenterally or in an aerosol form. The animals and poultry were re-vaccinated 3–6 months following the first vaccination, at the time of intense reproduction, or for special indications (outbreaks of forage poisoning, etc.).

In cases of urgent prophylaxis of anaerobic enterotoxemia of newborns, when the vaccination of the mother is useless, the newborns of non-vaccinated mothers are given the vaccine. The vaccination is done in two injections.

The vaccine does not produce any harmful effect on the vaccinated animal or the posterity. It is harmfull and areactogenic. The newborn animals are healthy, strong, viable, and gain weight quickly. The vaccine proves quite effective against the diseases caused by Clostridium perfringens types A, B, and D, Cl. oedematiens, Cl. septicum, Cl. titani, and Cl. botulinum. The efficacy is hundred percent. At the same time, all animals in the control group (100 percent) were affected by the disease and from 80 to 100 percent animals perished.

The vaccine remains effective up to five years.

The proposed vaccine for prophylaxis and treatment of clostridiosis in animals and poultry is prepared as follows.

A growth medium containing sources of nitrogen, carbon, phosphorus and mineral salts is inoculated with separate cultures of Clostridium perfringens types A, B, and D, Cl. oedematiens, Cl. septicum, Cl. tetani, and Cl. botulinum types A, B, C, E, and F. The cultures are grown under anaerobic conditions at a temperature of 35°–38° C., the pH of the medium being 5–10. The time of cultivation depends on the species and type of the microorganisms and averages from two hours to ten days. At the end of the cultivation period, a culture suspension of each species and type is separated into the culture filtrate and the microbial mass.

The activity of toxins, expressed in MLD per ml for albino mice is as follows:

| toxin of Cl. perfringens type A | 800–1200 |
|---|---|
| toxin of Cl. perfringens type B | 1000– 000 |
| toxin of Cl. perfringens type D | 1000–3000 |
| toxin of Cl. oedematiens | 12,000–20,000 |
| toxin of Cl. septicum | 800–1000 |

The culture filtrate containing the toxin is separated and passed through a Seitz filter. Then, the toxin is partially detoxicated by adding 0.4–0.5 percent by volume of a 40 percent formaldehyde solution into the culture filtrate at a temperature of 37°–38° C., the pH of the medium being 7–7.2. Formaldehyde is added in portions, once or twice within 1–20 days, depending on the species and the type of the microorganism producing the toxin. The only exception are toxins of Cl. perfringens type B, Cl. oedematiens and Cl. septicum, that are fully attenuated with formaldehyde within 1 to 30 days to give the toxoid.

The partially attenuated toxin or toxoid is then concentrated and purified by precipitating with a 45–60 percent solution of ammonium sulphate or sodium hexametaphosphate in the presence of IN hydrochloric acid. The precipitated toxin or toxoid is dissolved in a mixture of a phosphate buffer and physiological salt solution taken in the weight ratio of 1:1. The obtained solution is sterilized by passing through Seitz filters. Adding a 40 percent formaldehyde solution to the partly attenuated toxin at a temperature of 37°–38° C. converts it into the toxoid.

The obtained toxoid is tested for specific harmlessness on guinea pigs, and its antigenic activity, expressed in combining units, is determined. The toxoid is also tested for sterility.

Thus obtained monotoxoids, separated from the microbial cells, are mixed together and adsorbed on aluminium hydroxide gel.

If necessary, a preservative may be added to the prepared vaccine, such as a solution of sodium merthiolate (1:10,000).

The prepared vaccine is tested for sterility, toxicity, $Al_2O_3$ content, and immunogenecity.

The proposed vaccine possesses high antigenic and immunogenic properties and produces in vaccinated animals an effective antitoxic immunity to all said causative agents. The immunity persists from 1 to 2 years. The immunity to specific agents can last to 5 years. The vaccine dose is reduced two times. The titers of antitoxins in animals toward all monotoxoids increase 8–10 times, and the antitoxins are produced twice as fast. Following the primary immunization, the animals are re-vaccinated only once in their lifetime or only for special epizootic indications (an intervals from 2 to 5 years). The intensity of the immunity is 15–20 times higher than that attained with the known polyvalent toxoid-vaccine. The preparation is harmless and areactogenic for both vaccinated animals and man (milk and meat of vaccinated animals). The time of expiration of the vaccine has increased to five years.

Compared with the known preparations, the proposed vaccine is free from ballasts (microbial cells, non-specific proteins). The activity of the vaccine is determined by the combining units and is controlled at all stages of its production and use, which guarantees efficacy of the vaccine. The method of testing the vaccine, especially for immunogenecity and safety has been improved as well.

The use of the proposed vaccine for prophylactic purposes at affected farms, especially at large industrialized complexes, has proved its universal properties since it can effectively be used for vaccination of all animals or poultry against 5–11 widely spread natural causative agents, the vaccination dose being small. The vaccine protects females from forage poisoning, wound complications, and complications following the delivery. The vaccine can also be used for prophylaxis and treatment of saplings from anaerobic enterotoxemia, through the agency of colostrum of their mothers, guarantees complete cure of diseased animals and specific prophylxis of the mothers themselves against said causative agents, the efficacy being 100 percent. Rare cases of infections are not serious and the symptomatic treatment ensures rapid cure. Animals borne from vaccinated mothers are viable, strong, and rapidly gain weight. The use of the proposed vaccine at affected animal farms ensures rapid eradication of the diseases. At large animal breeding farms, the vaccine ensures the formation of the herd free from 5–11 widely spread natural causative agents that otherwise are the cause of considerable loss.

For a better understanding of the invention, the following examples of its practical embodiment are given by way of illustration.

EXAMPLE 1

Ten liters of a casein growth medium sterilized at a temperature of 112° C. for thirty minutes are inoculated with the culture Clostridium perfringens type A, taken in a quantity of 2 percent of the growth medium volume. The cultivation is carried out under anaerobic conditions at a temperature of 38° C. for 2–10 hours at pH of the medium of 5–10. The same casein medium is used for parallel cultivation of Cl. perfringens types B, D, Cl. oedematiens, Cl. septicum, Cl. tetani, and Cl. botulinum types A, B, C, D, E, and F. All cultures are grown separately by the described method except that the time of cultivation for each culture is from 2 hours to 10 days.

At the end of cultivation, 12 liters of the suspension of each culture are separated into the culture filtrate and the microbial mass. The culture filtrate (11.5 liters) containing the toxin is separated and passed through a Seitz filter. The toxin is then detoxicated with a 40 percent formaldehyde solution.

The toxin of Clostridium perfringens type A is partly detoxicated with a 40 percent formaldehyde solution at a temperature of 37°–38° C. for 14 days. Formaldehyde is added in two portions (0.2 percent by volume in each portion) at a 24-hour interval.

The toxin of Cl. perfringens type B is detoxicated and converted into the corresponding toxoid with a 40 percent solution of formaldehyde at pH 7.0–7.2, at a temperature of 37°–38° C., for 1–3 days. The entire portion of formaldehyde (0.4–0.5 percent by volume) is added at a time.

The toxin of *Cl. perfringens* type D is detoxicated partly with a 40 percent solution of formaldehyde at pH of the medium of 7–7.2, at a temperature of 37°–38° C., for 1–30 days, the required quantity of formaldehyde being added in two portions (0.2 percent by volume in each portion) at a 1–2 day interval.

The toxins of *Cl. oedematiens* and *Cl. septicum* are detoxicated and converted into the corresponding toxoids by the same procedure as described for *Cl. perfringens* type B.

The attenuated toxin or toxoid obtained from the culture filtrate (11.6 liters) is purified and concentrated by precipitating with a 25 percent solution of sodium hexametaphosphate, taken in a quantity of 0.5–1 percent by volume, in the presence of 1N hydrochloric acid at pH of 3.0–3.8.

The precipitated toxin or toxoid (100 g) is dissolved in three liters of a mixture of a phosphate buffer and a physiological salt solution (1:1), and the obtained solution is sterilized by passing it through Seitz filters.

The resultant products are concentrated solutions (separated from microbial cells) of toxoids of *Cl. perfringens* type B, *Cl. oedematiens*, *Cl. septicum*, and concentrated solutions of partly detoxicated toxins of *Cl. perfringens* types A and D.

The concentrated solution of partly detoxicated *Cl. perfringens* type A is converted into the corresponding toxoid by adding 0.2 percent by volume of a 40 percent formaldehyde solution in the course of 14–20 days.

The partly detoxicated toxin of *Cl. perfringens* type D is converted into the toxoid by a procedure similar to that described for *Cl. perfringens* type A.

The obtained monotoxoids, separated from microbial cells, are tested for sterility, toxicity, specific properties, and antigenic activity.

The antigenic activity of concentrated solution of each toxoid, separated from microbial cells, expressed in combining units per ml of solution, is as follows:

| toxoid of *Cl. perfringens* type A | 350 |
|---|---|
| toxoid of *Cl. perfringens* type B | 300 |
| toxoid of *Cl. perfringens* type D | 500 |
| toxoid of *Cl. oedematiens* | 500 |
| toxoid of *Cl. septicum* | 200 |

The concentrated solutions separated from microbial cells, prepared as described above, are diluted with a physiological salt solution (0.85 percent sodium chloride solution) to obtain solutions having the following antigenic activities expressed in the combining units per ml of the vaccine:

| toxoid of *Cl. perfringens* type A | 2 |
|---|---|
| toxoid of *Cl. perfringens* type B | 2 |
| toxoid of *Cl. perfringens* type D | 1 |
| toxoid of *Cl. oedematiens* | 1 |
| toxoid of *Cl. septicum* | 2 |

To prepare 2.5 l of the vaccine according to the invention, 200 ml of dilute solutions of each monotoxoid, having said antigenic activity, are mixed together, and alumina gel is added (400 ml as $Al_2O_3$).

The finished vaccine contains the following components having the following antigenic activity, expressed in combining units per ml of the vaccine:

| toxoid of *Cl. perfringens* type A | 2 |
|---|---|
| toxoid of *Cl. perfringens* type B | 2 |
| toxoid of *Cl. perfringens* type D | 1 |
| toxoid of *Cl. oedematiens* | 1 |
| toxoid of *Cl. septicum* | 2 |
| alumina gel (as $Al_2O_3$) | 1 ml |
| mixture of phosphate buffer and physiological salt solution (1:1) | balance. |

The finished vaccine is tested by known methods for completeness of sorption, sterility, toxicity, and immunogenecity (on mice). The vaccine is sterile, harmless, and immunogenic.

In order to prevent development of enterotoxemia in young pigs and calves at farms where 100 percent of the animals were affected with the disease (against the background of dyspepsia), the mortality rate being 50–80 percent, all adult female cattle and pigs were immunized with the vaccine.

The development of the disease in the young stock was as follows profuse diarrhea on the 2nd or 3rd day following the birth, sometimes with blood in the feces, the animals abstained from food, lost weight quickly and died within 2–3 days. In female animals, endometrites and mastites were observed.

The vaccine was used to immunize 100 pregnant cows and 150 pigs. The vaccine was given parenterally, 5 ml in two injections. The control group contained 20 cows and 50 pigs. The immunized animals delivered 95 calves and 1200 gilts. Fifty young calves got the disease in a mild form and ten of them perished. The affected gilts were 50 as well, and 25 of them perished.

All animals in the control group were affected by the disease, and a hundred percent mortality was observed with the calves and gilts born from the control animals.

EXAMPLE 2

The vaccine contains the following components, their antigenic activity, expressed in combining units per ml, being as follows:

| toxoid of *Cl. perfringens* type A | 10 |
|---|---|
| toxoid of *Cl. perfringens* type B | 10 |
| toxoid of *Cl. perfringens* type D | 5 |
| toxoid of *Cl. oedematiens* | 4 |
| toxoid of *Cl. septicum* | 10 |
| alumina gel | 5 mg (as $Al_2O_3$) |
| mixture of phosphate buffer and physiological salt solution (1:1) | balance. |

The vaccine is prepared by a procedure similar to that described in Example 1.

The finished preparation is sterile, harmless, and immunogenic. It is used for prophylaxis and treatment of calves and gilts with anaerobic enterotoxemia against the background of dyspepsia. The clinic of the disease is similar to that described in Example 1.

The vaccine was used to immunize 100 cows and 230 pigs in pregnancy. The vaccine was given pareneterally in a dose of 5 ml in two injections. The control group contained 20 cows and 30 pigs. The immunized animals delivered 97 calves and 1796 gilts. The disease did not develop, and none of the young stock perished. The non-immunized cows gave 18 calves, all of them had the grave form of the disease and 12 calves perished. The non-immunized pigs gave 205 gilts, 200 of them got the disease and 150 perished.

EXAMPLE 3

The vaccine contains the following components, their antigenic activity, expressed in combining unit per ml, being as follows:

| | |
|---|---|
| toxoid of *Cl. perfringens* type A | 100 |
| toxoid of *Cl. perfringens* type B | 100 |
| toxoid of *Cl. perfringens* type D | 80 |
| toxoid of *Cl. oedematiens* | 80 |
| toxoid of *Cl. septicum* | 100 |
| alumina gel | 10 mg (as $Al_2O_3$) |
| mixture of phosphate buffer and physiological salt solution (1:1) | balance. |

The proposed vaccine is prepared by the method described in Example 1.

The preparation is sterile, harmless, immunogenic and can be used for prophylaxis and treatment of young animals (calves, pigs) with anaerobic enterotoxemia against the background of dyspepsia, the clinic of the disease being similar to that described in Example 1.

The proposed vaccine was used to immunize 50 cows and 100 pigs in pregnancy. The vaccine was given in two injections in a dose of 5 ml. The control group contained 20 cows and 50 pigs. The immunized animals produced 50 calves and 960 gilts. 25 gilts developed the disease and 10 of them perished. 25 calves developed the disease in the mild form and ten of them perished. 200 young pigs were slightly affected and 50 of them perished.

One hundred percent of the animals in the control group got the disease.

All animals delivered by the non-immunized cows and pigs in the control group developed the disease and perished.

EXAMPLE 4

The vaccine contains the following components their antigenic activity, expressed in combining units per ml, being as follows:

| | |
|---|---|
| toxoid of *Cl. perfringens* type A | 2 |
| toxoid of *Cl. perfringens* type B | 2 |
| toxoid of *Cl. perfringens* type D | 1 |
| toxoid of *Cl. oedematiens* | 1 |
| toxoid of *Cl. septicum* | 2 |
| toxoid of *Cl. tetani* | 1 |
| alumina gel | 1 mg (as $Al_2O_3$) |
| mixture of phosphate buffer and physiological salt solution (1:1) | balance. |

The finished preparation is tested by the known methods for sterility, toxicity, and immunogenecity.

The vaccine is sterile, harmless, and immunogenic.

In order to prevent and treat anaerobic enterotoxemia of young cattle, pigs, sheep, horses, of endometritis, vaginitis, mastitis, wound complications, malignant edema, bradzot, of sheep, etc., the animals at farms affected with the diseases were immunized with the proposed vaccine. The disease among females was characterized by purulent discharges from the uterus and vagina, mastitis, miscarriages, malignant edema, about 50 to 70 percent animals being affected by the diseases. The disease in the young animals manifested in grave anaerobic enterotoxemia, the clinic being the same as described in Example 1, associated with grave nerve affections and resulting in 100 percent mortality among the newborns who perished within the first 3 days.

The vaccine was given to 200 cows, 219 pigs, 120 sheep and 80 horses in pregnancy. The preparation was given in two injections in a dose of 5 ml which was injected from one to three times, depending on the epizootic situation. The control group contained 20 pigs, 20 sheep, 20 horses and 20 cows. The immunized 150 pigs delivered 1350 gilts, the horses gave 60 foals, the sheep gave 150 lambs, and the cows gave 198 calves. The mild form of the disease was observed in 79 gilts, and the grave form in 70 gilts; 28 of them perished. The mild form developed in 30 foals and two of them perished. 60 lambs got diseased and 5 of them perished. The prophylactic use of the proposed vaccine in female animals to prevent endometritis, vaginitis, miscarriages and wound complications was effective in 75 percent. cases. The diseases were not eradicated in the control group.

Hundred percent young animals born from the non-immunized mothers, developed the disease and perished.

EXAMPLE 5

The vaccine contains the following components, their antigenic activity, expressed in combining units per ml., being as follows:

| | |
|---|---|
| toxoid of *Cl. perfringens* type A | 10 |
| toxoid of *Cl. perfringens* type B | 10 |
| toxoid of *Cl. perfringens* type D | 5 |
| toxoid of *Cl. oedematiens* | 4 |
| toxoid of *Cl. septicum* | 10 |
| toxoid of *Cl. tetani* | 5 |
| alumina gel | 5 mg (as $Al_2O_3$) |
| mixture of phosphate buffer and physiological salt solutions (1:1) | balance. |

The vaccine is prepared by a procedure similar to that described in Example 1. The finished preparation is sterile, harmless, and immunogenic, and it can be used for prophylaxis and treatment of young livestock (lambs, foals, calves, gilts, etc.) and female adults. The vaccine is effective against the diseases indicated in Example 4.

The proposed vaccine was used to immunize 242 pigs, 200 sheep, 150 horses, and 400 cattle in pregnancy. The preparation was given parenterally in a dose of 5 ml (from 1 to 3 times), depending on the epizootic situation. The control group contained 24 animals of each species. The immunized animals gave 1630 gilts, 180 lambs, 80 foals, and 389 calves. All young animals survived and none of them got the disease. The same picture was observed with the adults immunized with the vaccine. The diseases were not eradicated among the animals in the control group. Hundred percent animals born from the non-immunized mothers got the disease and perished.

EXAMPLE 6

The vaccine contains the following components, their antigenic activity, expressed in combining units per ml, being as follows:

| | |
|---|---|
| toxoid of *Cl. perfringens* type A | 10 |
| toxoid of *Cl. perfringens* type B | 10 |
| toxoid of *Cl. perfringens* type D | 5 |
| toxoid of *Cl. oedematiens* | 4 |
| toxoid of *Cl. septicum* | 10 |
| toxoid of *Cl. tetani* | 5 |
| toxoid of *Cl. botulinum* type A | 10 |

-continued

| | |
|---|---|
| toxoid of Cl. botulinum type B | 2 |
| toxoid of Cl. botulinum type C | 2 |
| toxoid of Cl. botulinum type D | 2 |
| toxoid of Cl. botulinum type E | 2 |
| toxoid of Cl. botulinum type F | 2 |
| alumina gel | 5 mg (as Al$_2$O$_3$) |
| mixture of phosphate buffer and physiological salt solution (1:1) | balance. |

The vaccine is prepared by a procedure similar to that described in Example 1.

The finished preparation is sterile, harmless, and immunogenic.

The vaccine was used to immunize commercial animals and poultry in order to prevent and treat forage toxicoinfections, wound complications, gas gangrene, post-labour complications, and enterotoxemia at animal and poultry farms affected with the diseases. The affection of the animals and poultry was characterized by signs of poisoning and quick lethal outcomes.

Said vaccine was used to immunize 200 minks, 500 birds and 150 pigs. The preparation was given to minks in a single injection of 1-2 ml with subsequent re-vaccination, or in aerosol form (2-3 ml). Pigs were immunized twice with 5 ml doses. The parenteral dose to hens and ducks was 0.5-2 ml, which was given 1 or 2 times, depending on the epizootic situation, or in aerosol form (1-3 ml). The control group contained 100 minks, 250 birds and 20 pigs. The immunized minks delivered 150 cubs and the pigs delivered 1350 gilts without any signs of the disease in the mothers and young animals, and all of them survived. A mild form of the disease was observed with 10-15 percent immunized birds. The disease was only transient (1-2 days), without lethal outcomes.

The disease affected 95 percent of the minks, poultry and pigs, including the mothers and young animals, in the control group, and 95 percent of them perished.

EXAMPLE 7

The vaccine contains the following components their antigenic activity, expressed in combining units per ml, being as follows:

| | |
|---|---|
| toxoid of Cl. perfringens type A | 10 |
| toxoid of Cl. perfringens type B | 10 |
| toxoid of Cl. perfringens type D | 5 |
| toxoid of Cl. oedematiens | 4 |
| toxoid of Cl. septicum | 10 |
| toxoid of Cl. tetani | 5 |
| toxoid of Cl. botulinum type A | 10 |
| toxoid of Cl. botulinum type C | 2 |
| alumina gel | 5 mg (as Al$_2$O$_3$) |
| mixture of phosphate buffer and physiological salt solution (1:1) | balance. |

The proposed vaccine is prepared by the method described in Example 1.

The finished preparation is sterile, harmless, and immunogenic. It is used for prophylaxis and treatment of commercial animals and poultry and is effective against the diseases indicated in Example 6.

Said vaccine was used to immunize 150 minks and 300 birds. The minks were given the vaccine in a single injection of 1-2 ml with subsequent re-vaccination, or in aerosol form (2-3 ml). Poultry (hens and ducks) were given 0.5-2 ml of the vaccine, from 1 to 2 times, depending on the epizootic situation. The control group contained 50 minks and 100 birds. The immunized minks delivered 100 cubs without any signs of the disease. All of them survived. The posterity of the immunized poultry was not affected by the disease either, and all chicks survived. About 90-100 percent of the non-immunized minks and poultry developed the diseases and perished.

What is claimed is:

1. A universal vaccine for prophylaxis and treatment of clostridiosis of animals and poultry, comprising formaldehyde-detoxicated toxoids of *Clostridium perfringens* types A, B, and D, *Cl.oedematiens* and *Cl.septicum* separated from the microbial mass, a sorbent comprised of a aluminum gel and a solvent comprised of phosphate buffer and physiological salt solution in a weight ratio of about 1:1, said vaccine being substantially free of bacterial cells and nonspecific proteins, the antigenic activity of said components, expressed in combining units per ml of the vaccine being as follows:

| | |
|---|---|
| toxoid of Cl. perfringens type A | 2-100 |
| toxoid of Cl. perfringens type B | 2-100 |
| toxoid of Cl. perfringens type D | 1-80 |
| toxoid of Cl. oedematiens | 1-80 |
| toxoid of Cl. septicum | 2-10 mg |
| sorbent | 1-10 mg |
| solvent | balance. |

2. A vaccine according to claim 1, which also contains a toxoid of *Cl.tetani*, separated from the microbial mass, its antigenic activity, expressed in combining units per ml of the vaccine, being 1-80.

3. A vaccine according to claim 2, which also contains toxoids of *Cl.botulinum* of at least two of the types A, B, C, D, E, and F, separated from the microbial mass, their antigenic activity, expressed in combining units per ml of the vaccine, being as follows:

| | |
|---|---|
| toxoid of Cl. botulinum type A | 2-100 |
| toxoid of Cl. botulinum type B | 0.2-80 |
| toxoid of Cl. botulinum type C | 0.2-80 |
| toxoid of Cl. botulinum type D | 0.2-80 |
| toxoid of Cl. botulinum type E | 0.2-80 |
| toxoid of Cl. botulinum type F | 0.2-80 |

4. A vaccine according to claim 1, containing a mixture of a phosphate buffer and a physiological salt solution, taken in the weight ratio of 1:1, as the solvent.

5. A vaccine according to claim 1, containing alumina gel as the sorbent.

6. A method for prophylaxis and treatment of clostridiosis of animals, and poultry, comprising treating said animals and poultry with a vaccine in a dose of 0.5 to 5 ml, from one to three times, the vaccine comprising toxoids of *Clostridium perfringens* types A, B, and D, *Cl.oedematiens*, and *Cl. septicum*, separated from the microbial mass, a sorbent comprised of aluminum gel and a solvent comprised of phosphate buffer and physiological salt solution in a weight ratio of about 1:1, said vaccine being substantially free of bacterial cells and nonspecific proteins the antigenic activity of said toxoids, expressed in combining units per ml of the vaccine, being as follows:

| | |
|---|---|
| toxoid of Cl. perfringens type A | 2-100 |
| toxoid of Cl. perfringens type B | 2-100 |
| toxoid of Cl. perfringens type D | 1-80 |
| toxoid of Cl. oedematiens | 1-80 |
| toxoid of Cl. septicum | 2-100 |

| | |
|---|---|
| sorbent | 1–10 mg |
| solvent | balance | with subsequent re-vaccination.

7. A method for prophylaxis and treatment of clostridiosis according to claim 6, in which said animals and poultry are given said vaccine also containing a toxoid of *Cl.tetani*, separated from the microbial mass, its antigenic activity, expressed in combining units per ml of the vaccine, being 1–80.

8. A method for prophylaxis and treatment of clostridiosis according to claim 6, in which said animals and poultry are given the vaccine also containing toxoids of *Cl.botulinum* of at least two of the types A, B, C, D, E, and F, separated from the microbial mass, their antigenic activity, expressed in combining units per ml of the vaccine, being as follows:

| | |
|---|---|
| toxoid of *Cl. botulinum* type A | 2–100 |
| toxoid of *Cl. botulinum* type B | 0.2–80 |
| toxoid of *Cl. botulinum* type C | 0.2–80 |
| toxoid of *Cl. botulinum* type D | 0.2–80 |
| toxoid of *Cl. botulinum* type E | 0.2–80 |
| toxoid of *Cl. botulinum* type F | 0.2–80. |

9. A method for prophylaxis and treatment of clostridiosis according to claim 6, in which said animals and poultry are given said vaccine parenterally.

10. A method for prophylaxis and treatment of clostridiosis according to claim 6, in which said animals and poultry are given the vaccine in an aerosol form.

11. A vaccine according to claim 1 which has an expiration time of about 5 years.

12. A method according to claim 1 wherein immunity to said clostridiosis lasting about 1 to 2 years is provided.

* * * * *